United States Patent [19]
Glazer et al.

[11] Patent Number: 5,776,744
[45] Date of Patent: Jul. 7, 1998

[54] METHODS AND COMPOSITIONS FOR EFFECTING HOMOLOGOUS RECOMBINATION

[75] Inventors: Peter M. Glazer, Guilford, Conn.; L. Michael Lin, Wilmington, Del.; Jay George, Gaithersburg, Md.

[73] Assignees: Yale University, New Haven, Conn.; Codon Pharmaceuticals, Inc., Gaithersburg, Md.

[21] Appl. No.: 467,126

[22] Filed: Jun. 7, 1995

[51] Int. Cl.⁶ .............. C12N 15/63; C12Q 1/70; C12Q 1/68; C12P 19/34
[52] U.S. Cl. .............. 435/172.3; 435/5; 435/6; 435/91.1; 435/91.2
[58] Field of Search .............. 435/6.5, 91.1, 435/91.2, 172.3

[56] References Cited

FOREIGN PATENT DOCUMENTS

WO 92/08791  5/1992  WIPO.

OTHER PUBLICATIONS

Kim et al. "Probing the structure of a putative intermediate in homologous recombination: The third strand in the parallel DNA triplex is in contact with the major groove of the duplex", J. Mol. Biol. 247:874–889, 1995.

Camerini–Otero et al, "Parallel DNA triplexes, homologous recombination and other homology dependent DNA interactions", Cell 73:217–223, Apr. 1993.

Rao et al, "Homologous recognition and triplex formation promoted by RecA protein between duplex oligonucleotides and single–stranded DNA", J. Mol. Biol. 229:228–343, 1993.

Sandor et al. "Triple helix directed psoralen adducts induce a low frequency of recombination in an SV40 shuttle vector", Biochimica et Biophysica Acta 1263:235–240, Sep. 1995.

Wang et al. "Targeted mutagenesis in mammalian cells mediated by intracellular triple helix formation", Mol. Cell. Biol. 15(3): 1759–1768, Mar. 1995.

Rooney et al. "Antiparallel, intramolecular triplex DNA stimulates homologous recombination in cells", Proc. Natl. Acad. Sci. 92:2141–2144, Mar. 1995.

Kim et al, "Parallel DNA triplexes and homologous recombination", in Structural Biology: The State of the Art, Proceedings of the Eighth Conversation, Adenine Press, Albany, New York, pp. 67–74, 1994.

*Primary Examiner*—W. Gary Jones
*Assistant Examiner*—Jeffrey Fredman
*Attorney, Agent, or Firm*—Glenn E. Karta

[57] ABSTRACT

Methods, compositions and kits for effecting homologous recombination are described. In one aspect, the method utilizes two introduced DNAs: (1) a mutagen–linked single–stranded oligonucleotide capable of specifically binding to double-stranded DNA to form a triple-stranded helix, and (2) a donor DNA fragment capable of undergoing homologous recombination with DNA targeted by the oligonucleotide.

34 Claims, 4 Drawing Sheets

METHODS AND COMPOSITIONS FOR EFFECTING HOMOLOGOUS RECOMBINATION

BACKGROUND OF THE INVENTION

1. Field of the Invention

This invention relates to targeting mutagen-linked third strands, or unmodified third strands that bind with high affinity to a target region associated with double-stranded native nucleic acid sequences, to induce DNA damage to stimulate homologous recombination with an introduced donor nucleic acid strand. In particular, the invention provides a method for effecting gene transfer, gene alteration or mutation repair at a specific sequence site on the native DNA.

2. Description of Related Art

Third Strands and Triple-Stranded DNA

Oligonucleotides (third strands) can bind to double-stranded DNA to form triple-stranded helices (triplexes) in a sequence specific manner (Beal and Dervan, *Science* 251: 1360 (1991); Beal and Dervan, *Nucleic Acids Res.*, 20:2773 (1992); Broitman and Fresco, *Proc. Natl. Acad. Sci. USA*, 84:5120 (1987); Fossella, et al., *Nucleic. Acids Res.* 21:4511 (1993); Letai et al., *Biochemistry* 27:9108 (1988); Sun, et al., *Proc. Natl. Acad. Sci. USA* 86:9198 (1989)).

Oligonucleotide-mediated triplex formation has been shown to prevent transcription factor binding to promoter sites and to block mRNA synthesis in vitro and in vivo (Blume et al., *Nucleic Acids Res.* 20:1777 (1992); Cooney, et al., *Science* 241:456 (1988); Duval-Valentin, et al., *Proc. Natl. Acad. Sci. USA* 89:504 (1992); Grigoriev, et al., *Proc. Natl. Acad. Sci. USA* 90:3501 (1993); Grigoriev, et al., *J. of Biological Chem.* 267:3389 (1992); Ing, et al., *Nucleic Acids Res.* 21:2789 (1993); Maher, et al., *Science* 245:725 (1989); Orson, et al., *Nucleic Acids Res.* 19:3435 (1991); Postel, et al., *Proc. Natl. Acad. Sci. USA* 88:8227 (1991); Young, et al., *Proc. Natl. Acad. Sci. USA* 88:10023 (1991)). Such inhibition of expression, however, is transient, depending on the sustained presence of the oligonucleotides. It also depends on the stability of the triple helix, which can be disrupted by transcription initiated at nearby sites (Skoog and Maher, *Nucleic. Acids Res.* 21:4055 (1993)). To overcome these problems, methods to prolong oligonucleotide-duplex interactions using DNA intercalating or cross-linking agents have been explored in experiments to block transcription initiation or elongation (Grigoriev, et al., *Proc. Natl. Acad. Sci. USA* 90:3501 (1993); Grigoriev, et al., *J. of Biological Chem.* 267:3389 (1992); Sun, et al., *Proc. Natl. Acad. Sci. USA* 86:9198 (1989); Takasugi, et al., *Proc. Natl. Acad. Sci. USA*, 88:5602 (1991)).

Instead of using third strands to transiently block gene expression, the present invention utilizes third strands to target or direct homologous recombination to specific sites in or near selected genes in order to produce permanent, heritable changes in gene function and expression. In this approach, DNA modification or damage that stimulates homologous recombination is directed to a selected site.

Third-Strand Pharmacokinetics

Sufficient pharmacokinetic studies of oligonucleotides in cell culture and in vivo have been carried out to indicate utility as therapeutic agents. The studies include native phosphodiester backbones as well as analog phosphorothioate and methlyphosphonate backbones. Pharmacokinetics and toxicology literature up to 1991 have been thoroughly reviewed in Crooke (Anti-Cancer Drug Design, 6: 609 (1991)). A more recent summary may be found in Stein and Cheng, Science, 261: 1004–1012 (Aug. 20, 1993).

Phosphodiester (150 µM), phosphorothioate (25 µM) and methylphosphonate (150 µM) oligonucleotides are non-toxic to cells in culture exposed to the oligonucleotides up to 3 days (see the Crooke review). These sub-toxic concentrations are 10- to 100- times higher than the concentrations which cause maximum DNA damage in this invention (see Table 3 in Example 4), which leads to a more than acceptable therapeutic window regarding toxicity.

Studies show favorable uptake of oligonculeotides in cell culture. Two examples are: A fluorescently-labelled phosphodiester homopolymer of thymine of 15 bases in length (15-mer) showed 80% internalization in 2–3 hours (Stein, et al., Biochemistry, 32: 4855 (1993). 3' amine modified oligonucleotides (31-mer and 38-mer) specific for an HIV mRNA applied to HIV infected human cells at a concentration of 5 µM, after 2 hours achieved nuclear concentrations of 4.5 µM to 6.1 µM (Zendegui, et al., *Nulceic Acids Res.*, 20:307 (1992). The higher than 5 µM intranuclear concentrations found in this study indicate that oligonucleotides preferentially collect in the nucleus, a result favorable for third-strand binding to chromosomal DNA in this invention.

The half-life inside cells in culture is also favorable with most oligonucleotide remaining intact up to 24 hours inside the cells (Zendegui, et al., *Nulceic Acids Res.*, 20:307 (1992). See also the Stein and Cheng review and references therein.

The pharmacokinetics, biodistribution and stability of oligonucleotides in mice has been thoroughly examined in two studies (Agrawal, et al., *Proc. Natl. Acad. Sci. USA*, 88:7595 (1991); and Zendegui, et al., *Nucleic Acids Res*, 20:307 (1992). The Agrawal and Zendegui studies used phorphorothioate (20-mer) and 3' amine modified phosphodiester (38-mer) oligonucleotides, respectively. While plasma clearance was fast in both studies (on the order of 10 minutes), oligonucleotide remained at least 50 % intact in most tissues for 8 to 48 hours. Since it takes only 2 hours for oligonucleotides to effectively internalize in the nucleus of cells, the over-8-hour tissue half-life in live mice is more than sufficient for the oligonucleotides to internalize in cells. Furthermore, the amounts of oligonucleotide collecting in tissue, 1 to 10 µM, are compatible with the amounts needed for therapy in this invention.

Stimulation of Homologous Recombination

A number of physical and chemical agents have been shown to stimulate homologous recombination between two sufficiently similar (homologous) DNA sequences in cultured mammalian cells. The agents include ultraviolet light, ionizing radiation, and mutagens and carcinogens such as 1-nitrosopyrene, psoralen, hydroxymethyl-trimethylpsoralen (HMT), and mitomycin C (Reardon, et al., *Nucleic Acids Res.*, 19: 4623 (1991); Bhattacharyya, et al., *Mol. and Cell. Biol.*, 10: 3945 (1990); Saffran, et al., *Mutation Res. and DNA Repair,* 274:1 (1992); Vos and Hanawalt, *Mol. and Cell. Biol.*, 9:2897 (1989)).

In a typical demonstration, two copies of a gene each defective at different sequence sites are transferred into a cell on a plasmid and reside there as extrachromosomal DNA. After a time, wild-type genes resulting from homologous recombination between the two defective genes are observed and quantified. The efficiency of recombination in extra-chromosomal DNA is high, with often 1–10% of the population transformed to wild-type. Linear DNA recombines more efficiently than circular DNA, and the DNA must be double stranded to recombine. Single-stranded DNA, however, may be introduced into the cell and recombination will occur if the complementary single-strands are also introduced into the cell so that double-stranded DNA can form. Cleaving DNA with restriction enzymes at appropriate locations will also stimulate homologous recombination, and these enzymes often are used in experimental demonstrations. (Reviewed in Lin, et al., in "Mechanisms of Eukaryotic Recombination", Academic Press: 15 (1992)). To use exogenous restriction enzymes in living cells to stimulate recombination requires, however, that they be introduced into the cells by some procedure such as electroporation.

Since the methods described above allow for recombination between two introduced defective genes and do not involve native chromosomal genes, they do not lend themselves to replacing defective genes, or constructing useful cell lines or transgenic animals. The methods are useful, however, as research tools to understand factors influencing the stimulation of homologous recombination.

Gene Targeting

"Gene targeting" is used to describe homologous recombination between a DNA introduced into cells and the native chromosomal DNA of the cells. It is perhaps inappropriately called gene targeting, because the introduced DNA is not targeted by the experimenter to the homologous chromosomal DNA. In a typical gene-targeting method, introduced DNA is transported into cells by electroporation, microinjection, calcium phosphate treatments, inside cationic liposomes, or by other standard methods, and the experimenter "passively" allows the natural cellular mechanisms to carry out the recombination event.

This passive gene targeting is generally highly inefficient, with typical observed recombination frequencies usually $10^{-5}$ or lower (targeted events per surviving cell), although in special systems the efficiency can be higher. In addition, random integration to chromosome sites not homologous to the introduced DNA (illegitimate or nonhomologous recombination) may overwhelm the legitimate or homologous recombination events by 1000-fold. In one recent instance, however, in the parasite *Toxoplasma gondii*, passive gene targeting produced about 50% homologous and 50% nonhomologus recombination, when the introduced DNA was 8 kilobases (kb) in size. In contrast, when the introduced DNA was<2 kb, nonhomologous recombination was overwhelmingly observed (Donald and Roos, *Mol. Biochem. Parasitol.*, 63: 243 (1994)).

While finding utility in the construction of transgenic animals and special cell lines (see, for example, Pfeffer and Mak, *Annu. Rev. Immunol.* 12:367 (1994); Sands, et al., *Mutation Res.*, 307: 557 (1994); Arbones, et al., *Nat. Genet.*, 6:90 (1994)), passive gene targeting nevertheless has limitations. The often low frequencies require methods of selecting transformed cells, so utility in producing transgenic animals is limited to cells which can be manipulated outside the animal such as embryonic stem cells.

In contrast, in the present invention, third-strand-directed nucleic acid modification or damage of the native nucleic acid homologous to the introduced nucleic acid is used to stimulate recombination. As a result, the frequencies of homologous recombination between a native nucleic acid segment in the cell and an introduced linear DNA fragment are high. In addition, the percentage of non-targeted recombination should be low as evidenced both by mutagenesis "footprints" of DNA damage by triple helix formation.

SUMMARY OF THE INVENTION

The present invention provides a method for effecting homologous recombination between a native nucleic acid segment in a cell and a donor nucleic acid segment introduced into the cell, which comprises:

a) introducing into a cell: i) an oligonucleotide third strand which comprises a base sequence capable of forming a triple helix at a binding region on one or both strands of a native nucleic acid segment in the vicinity of a target region where the recombination is to occur, said oligonucleotide being capable of inducing homologous recombination at the target region of the native nucleic acid, and ii) a donor nucleic acid which comprises a nucleic acid sequence sufficiently homologous to the native nucleic acid segment such that the donor sequence is capable of undergoing homologous recombination with the native sequence at the target region;

b) allowing the oligonucleotide to bind to the native nucleic acid segment to form a triple stranded nucleic acid, thereby inducing homologous recombination at the native nucleic acid segment target region; and c) allowing homologous recombination to occur between the native and donor nucleic acid segments.

Another aspect of the present invention concerns a method for effecting homologous recombination between a first nucleic acid segment in a cell and a donor nucleic acid segment introduced into the cell, which comprises:

a) contacting a donor nucleic acid segment with an oligonucleotide third strand which comprises a base sequence capable of forming a triple helix at a binding region on one or both strands of the donor nucleic acid segment in the vicinity of a target region where the recombination is to occur, said oligonucleotide being capable of inducing homologous recombination at the target region of the donor nucleic acid, and said donor having a sequence sufficiently homologous to a first nucleic acid segment such that the donor sequence will undergo homologous recombination with the first sequence at the target region;

b) allowing the oligonucleotide to bind to the donor nucleic acid segment to form a triple stranded nucleic acid, thereby treating the donor nucleic acid segment to make it capable of inducing homologous recombination at the donor nucleic acid segment target region;

c) introducing into a cell the treated donor nucleic acid; and d) allowing homologous recombination to occur between the first and donor nucleic acid segments.

In another aspect, the present invention provides a composition comprising:

a) an oligonucleotide third strand which comprises a base sequence which is capable of forming a triple helix at a binding region on one or both strands of a native nucleic acid segment in the vicinity of a target region, said oligonucleotide being capable of inducing homologous recombination at the target region of the native nucleic acid; and b) a donor nucleic acid which comprises a nucleic acid sequence sufficiently homologous to the native nucleic acid segment such that the donor nucleic acid will undergo homologous recombination with the native sequence at the target region when the third strand is bound to the native nucleic acid.

In yet another aspect, the present invention provides a kit, which comprises packaging material and:

a) an oligonucleotide third strand which comprises a base sequence which is capable of forming a triple helix at a binding region on one or both strands of a native nucleic acid segment in the vicinity of a target region, said oligonucleotide being capable of inducing homologous recombination at the target region of the native nucleic acid; and b) a donor nucleic acid which comprises a nucleic acid sequence sufficiently homologous to the native nucleic acid segment such that the donor nucleic acid will undergo homologous recombination with the native sequence at the target region when the third strand is bound to the native nucleic acid.

The present methods, compositions and kits are useful in research and therapeutic applications where recombination at a specific site is desired. The present inventions are also useful in plant agriculture, where they may be used to, for example, increase the protein nutrition of grains by replacing storage protein genes with genes which retain their ability to pack into seeds but provide proteins with more limiting essential amino acids such as lysine and tryptophan; adding genes with new functions such as insect resistance; and increasing the expression of genes with useful properties.

DETAILED DESCRIPTION OF THE INVENTION

Oligonucleotide

Figure 1:
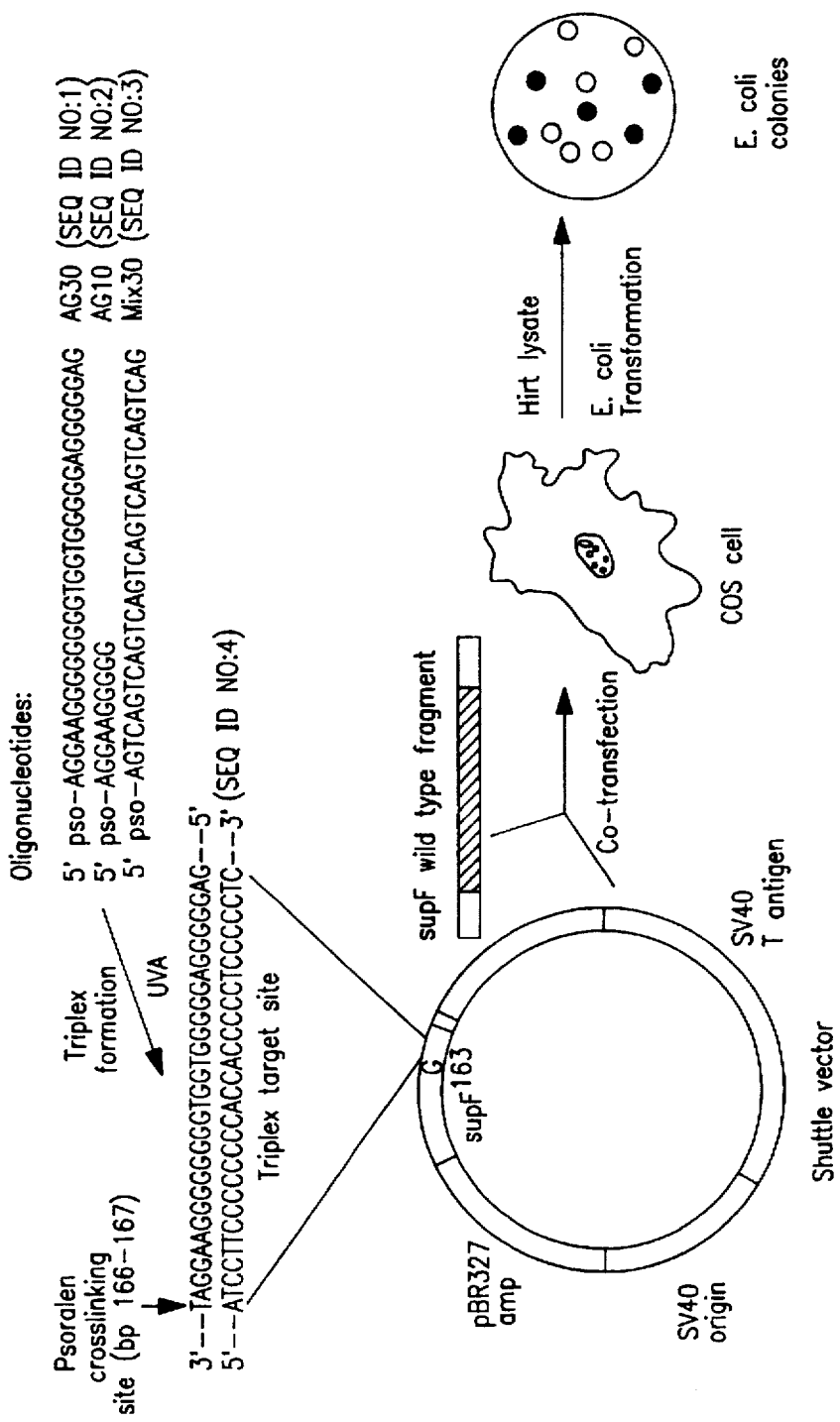
FIG. 1 schematically illustrates the experiment demonstrating homologous recombination between a wild type supF gene fragment and the psupFG1 shuttle vector which were co-transfected into COS cells.

The oligonucleotide third strand is a synthetic or isolated oligonucleotide capable of binding with specificity to a predetermined binding region of a double-stranded native nucleic acid molecule to form a triple-stranded structure. The third strand may bind solely to one strand of the native nucleic acid molecule, or may bind to both strands at different points along its length. The predetermined target region of the double-stranded nucleic acid is in or is adjacent to a gene, MRNA synthesis or processing control region, or other nucleic acid region that it is desirous to replace by homologous recombination. The predetermined binding region, if adjacent to the targeted region, is preferably within 10,000 nucleotides or bases from the targeted region.

Preferably, the oligonucleotide is a single-stranded DNA molecule between about 7 and about 50, most preferably between about 10 and about 30 nucleotides in length. The base composition can be homopurine, homopyrimidine, or mixtures of the two. The third strand binding code and preferred conditions under which a triple-stranded helix will form are well known to those skilled in the art (U.S. Pat. No. 5,422,251; Beal and Dervan, *Science* 251: 1360 (1991); Beal and Dervan, *Nucleic Acids Res.*, 20:2773 (1992); Broitman and Fresco, *Proc. Natl. Acad. Sci. USA*, 84:5120 (1987); Fossella, et al., *Nuc. Acids Res.* 21:4511 (1993); Letai, et al., *Biochemistry* 27:9108 (1988); Sun, et al., *Proc. Natl. Acad. Sci. USA* 86:9198 (1989)). Briefly, adenosine, uridine, thymidine and inosine in the third strand will bind to adenosine in the duplex, and guanosine, cytidine and inosine in the third strand will bind to guanosine in the duplex. The third strand need not be perfectly complementary to to the duplex, but may be substantially complementary. In general, by substantially complementary is meant that one mismatch is tolerable in every about 10 base pairs.

The oligonucleotide may have a native phosphodiester backbone or may be comprised of other backbone chemical groups or mixtures of chemical groups which do not prevent the triple-stranded helix from forming. These alternative chemical groups include phosphorothioates, methylphosphonates, peptide nucleic acids (PNAs), and others known to those skilled in the art. Preferably, the oligonucleotide backbone is phosphodiester.

The oligonucleotide may also comprise one or more modified sugars, which would be known to those skilled in the art. An example of such a sugar includes α-enantiomers.

The third strand may also incorporate one or more synthetic bases if such is necessary or desirable to improve third strand binding. Examples of synthetic base design and the bases so designed are found in the co-pending U.S. application of Fresco, et al. entitled "Residues for Binding Third Strands to Complementary Nucleic Acid Duplexes of any Base-Pair Sequence", filed concurrently herewith and bearing application Ser. No. 08/473,888.

If it is desired to protect the oligonucleotide from nucleases resident in the target cells, the oligonucleotide may be modified with one or more protective groups. In a preferred embodiment, the 3' and 5' ends may be capped with a number of chemical groups known to one of ordinary skill, such as alkyl amines, acridine, cholesterol, etc. In another embodiment, the oligonucleotide third strand may be protected from exonucleases by circularization.

The oligonucleotide third strand should be capable of inducing homologous recombination at a target region of the native nucleic acid. That may be accomplished by the binding of the third strand alone to the binding region of the native nucleic acid, or by a moiety attached to the oligonucleotide. In the embodiment where the binding of the third strand alone induces the recombination, the third strand should bind tightly to the binding region, i.e., it should have a low dissociation constant ($K_d$) for the binding region. The $K_d$ is estimated as the concentration of oligonucleotide at which triplex formation is half-maximal. Preferably, the oligonucleotide has a $K_d$ less than or equal to about $10^{-7}$ M, most preferably less than or equal to about $2 \times 10^{-8}$ M. The $K_d$ may be readily determined by one of ordinary skill, including estimation using a gel mobility shift assay (Durland, et al., *Biochemistry* 30, 9246 (1991); see also the copending U.S. application of Glazer entitled "Triple Helix Forming Oligonucleotides for Targeted Mutagenesis" filed concurrently herewith, the content of which is incorporated by reference.).

Mutagen

The oligonucleotide may be chemically modified to include a mutagen at either the 5' end, 3' end, or internal portion so that the mutagen is proximal to a site where it will cause modification or damage to the native nucleic acid. Preferably the mutagen is incorporated into the oligonucleotide during nucleotide synthesis. For example, commercially available compounds such as psoralen C2 phosphoroamidite (Glen Research, Sterling Va.) are inserted into a specific location within an oligonucleotide sequence in accordance with the methods of Takasugi et al., *Proc. Natl. Acad. Sci USA*, 88:5602 (1991); Gia et al., *Biochemistry* 31:11818 (1992); Giovannangeli, et al., *Proc. Natl. Acad. Sci. USA*, 89:8631 (1992), all of which are incorporated by reference herein.

The mutagen may also be attached to the oligonucleotide through a linker, such as sulfo-m-maleimidonbenzoly-N-hydroxysuccinimide ester (sulfo-MBS, Pierce Chemical Company, Rockford Ill.) in accordance with the methods of Liu et al., Biochem. 18:690 (1979) and Kitagawa and Ailawa, *J. Biochem.* 79:233 (1976), both of which are incorporated by reference herein. Alternatively, the mutagen is attached to the oligonucleotide by photoactivation, which causes a mutagen, such as psoralen, to bind to the oligonucleotide.

The mutagen can be any chemical capable of stimulating homologous recombination. Such stimulation can be caused by modifying the target nucleic acid in some way, such as by damaging with, for example, crosslinkers or alkylating agents. The mutagen may also be a moiety which increases the binding of the third strand to the target, such as intercalators (e.g., acridine). Such mutagens are well known to those skilled in the art. The chemical mutagen can either cause the mutation spontaneously or subsequent to activation of the mutagen, such as, for example by exposure to light.

Preferred mutagens include psoralen and substituted psoralens such as hydroxymethyl-psoralen (HMT) that require activation by ultraviolet light; acridine, bleomycin, fullerines, mitomycin C, polycyclic aromatic carcinogens such as 1-nitrosopyrene, alkylating agents; restriction enzymes, nucleases, radionuclides such as $^{125}I$, $^{35}S$ and $^{32}P$; and molecules that interact with radiation to become mutagenic, such as boron that interacts with neutron capture and iodine that interacts with auger electrons.

If necessary for activation of the mutagen, light can be delivered to cells on the surface of the body, such as skin cells, by exposure of the area requiring treatment to a conventional light source. Light can be delivered to cells within the body by fiber optics or laser by methods known to those skilled in the art. Targeted flourogens that provide sufficient light to activate the mutagens can also provide a useful light source. Ex-vivo exposure to light of cells such as embryonic stem cells can be carried out by procedures known to those skilled in the art of ex vivo medical treatments.

Donor Nucleic Acid

The donor nucleic acid is either a double-stranded nucleic acid, a substantially complementary pair of single stranded nucleic acids, or a single stranded nucleic acid. The sequence of the donor nucleic acid at its ends is substantially homologous to the nucleic acid region which is to be replaced by homologous recombination. Preferably, the region of substantial homology is at least about 20 bases at each end of the donor nucleic acid. By substantial homology is meant that at least about 85% of the available base pairs are matching.

The differences in base sequences between the donor nucleic acid and the targeted region it is desired to replace are base changes, deletions of bases or insertions of bases, nucleotide repeats, or a combination of these, chosen to accomplish the desired genetic and phenotypic change. Nucleic acid segments may be added according to the present invention. Such segments include a gene, a part of a gene, a gene control region, an intron, a splice junction, a transposable element, a site specific recombination sequence, and combinations thereof.

The donor nucleic acid strands, whether single- or double-stranded, may be gene sized, or greater or smaller. Preferably, they are at least about 40 bases in length, preferably between about 40 and about 1,000,000 bases in length. Most preferably, the lengths are between about 500 and about 3,000 bases.

The Native Nucleic Acid

The native nucleic acid to which the oligonucleotide third strand binds may be chromosomal or extrachromosomal. Examples of extrachromosomal DNA are well known, and include mitochondrial and episomal DNA, plasmids and chloroplasts.

Method of Administration of the Oligonucleotide

Experimental manipulations such as peptide-facilitated uptake, electroporation, micro-injection, microprojectiles, calcium phosphate or other treatments well known to those skilled in the art may be used to deliver the oligonucleotide to the nucleus of the target cell. Preferably, the oligonucleotide can be delivered to cells simply by exposing the cells to the oligonucleotide by including it in the medium surrounding the cells, or in live animals or humans by bolus injection or continuous infusion. The exact concentration will be readily determined by one of ordinary skill, and will depend on the specific pharmacology and pharmacokinetic situation. Typically, from about 0.1 to about 10 µM will be sufficient.

Modifying Donor Nucleic Acid

In another aspect of the invention, the nucleic acid modification or damage used to stimulate homologous recombination is targeted to the donor nucleic acid (as opposed to the native nucleic acid) either inside or outside the target cells. For the preferred embodiment where the nucleic acid modification or damage is effected outside the target cell, the modified or damaged donor nucleic acid is then introduced into the target cell to stimulate homologous recombination with the native nucleic acid.

Modifying or damaging the donor nucleic acid outside the cell has several desirable features including: nucleic acid modification or damage can be caused with higher efficiency outside the cell; mutagens and other treatments (e.g., psoralen-UVA) potentially toxic to the cell, animal or human can be used since the mutagen can be isolated away from the modified or damaged donor nucleic acid before the purified donor nucleic acid is introduced into the target cell; conditions (e.g., temperature, cation composition and concentration) can be controlled to maximize binding of third-strands for any binding motif; and nucleic acid modifying or damaging agents can be directly synthesized into specific sites on the donor nucleic acid by methods well known to those skilled in the art, without the use of third strands. In addition, to increase efficiency of and to control the location of modification or damage, third strand sites can be engineered into the donor nucleic acid at a location where the engineered nucleic acid segment is unlikely to cause unwanted effects when the donor nucleic acid is recombined into the organism's native nucleic acid.

Method of Administration of the Donor Nucleic Acid

The donor nucleic acid can be delivered to the nucleus of cells in culture or cells removed from an animal or a patient (ex vivo) by experimental manipulations such as peptide-facilitated uptake, electroporation, calcium chloride, micro-injection, microprojectiles or other treatments well known to those skilled in the art. For single-stranded donor nucleic acids of less than about 100 bases, the donor nucleic acid can be delivered to cells or live animals simply by exposing the cells to the oligonucleotide that is included in the medium surrounding the cells, or in live animals or humans by bolus injection or continuous infusion. One of the complementary single strands is delivered and the other delivered at the same time or up to 12 hours later, preferably about 20 to about 40 minutes later.

In whole animals, patients, or plants, since gene-size pieces of nucleic acid cannot enter cells without the usual experimental manipulations (e.g., without electroporation, calcium phosphate or other treatments), introduced nucleic acid in this invention may be delivered by usual therapeutic means, especially since the introduced nucleic acid in this invention may be smaller than gene size.

The donor nucleic acid may also be introduced into the cell in the form of a packaging system. Such systems include DNA viruses, RNA viruses, and liposomes as in traditional gene therapy.

Methods of Use

The invention provides a method for effecting gene transfer, mutation repair, and targeted mutagenesis at a specific sequence site on a native nucleic acid segment, either in cells or in a living organism.

Examples of therapeutic use are apparent. For example, if a targeted nucleic acid region contains base changes, deletions or additions of bases which cause an inherited or somatic genetic disorder, then the donor nucleic acid can provide a normal gene by replacing the defective nucleic acid to correct that disorder. If the targeted nucleic acid region is one which confers inherited or acquired susceptibility to a genetic disorder (e.g., cancer), the donor nucleic acid can reverse that susceptibility.

A preferred therapeutic use of the methods and compositions of the invention are in ex vivo therapies where third strands and donor nucleic acid can be introduced into target cells outside the body. Diseases amenable to ex vivo treatment include white blood cell diseases such as leukemias and red blood cell diseases such as sickle-cell anemia and β thalassemia. For additional discussion of those therapeutic uses, see the co-pending Glazer U.S. application entitled "Treatment of Hemoglobinopathies" filed concurrently herewith. The individual steps used in such therapies are well known to one of ordinary skill. For example, such steps include removing bone marrow from the patient, treating it with a donor nucleic acid and either a mutagen-linked third strand or third strand alone to stimulate homologous recombination, and returning the treated bone marrow to the patient's body. Therapies that remove, treat and return the patient's own bone marrow are called autologous bone marrow transplants (ABMT).

Within 40,000 bases of a site where it is desirous to introduce a nucleic acid modification to correct a disease-causing mutation, there will be on average $2 \times 40,000/2^{10}=78$ purine stretches of length 10 and even $2 \times 40,000/2^{15}=2$ purine stretches of length 15 to serve as targets for third-strand binding to stimulate homologous recombination. In addition, all the individual elements of AMBT therapy utilizing this invention have been demonstrated in one setting or another, as the following illustrates:

- In an ex vivo setting, both third strands and donor nucleic acids can be delivered by means used in the research laboratory such as, for example, electroporation (see Example 1).

- In clinical settings, the mutagen psoralen, for example, has been used for therapy—topically for dermatological conditions and ex vivo for bone marrow transplants to reduce the risk of graft-vs-host disease and as therapy for cutaneous T-cell lymphoma, and psoralen alone is relatively non-toxic in clinical use (Ortonne, *Clin. Dermatol.* 7:120 (1989); Taylor and Gasparro, *Semin. Hematol.* 29:132 (1992); Jampel, et al., *Arch. Dermatol.* 127: 1673 (1991); Ullrich, *J. Invest. Dermatol.* 96:303 (1991)).

- In cell culture, psoralen-linked and acridine-linked third strands are less toxic than the drugs administered alone (see Zerial, et al., *Nucleic Acids Res.* 15:9909 (1987).

- In a clinical setting, ABMT is increasingly used as a therapy for blood-related diseases such as leukemia, sickle-cell anemia and β thalassemia (Roberts, *Bone Marrow Transplant.* 14: 197 (1994); Apperley, *Bailliere's Clinical Haematology.* 6:299 (1993).

For some blood-related diseases, for example sickle cell anemia and β thalassemia, correction of only some of the defective genes will have a therapeutic effect and may even eliminate all severe disease symptoms as evidenced by the fact that expression of 15% or less fetal hemoglobin will render the diseases harmless (Bunn and Forget, "Hemoglobin: Molecular, Genetic and Clinical Aspects, 5th Ed. W.B. Saunders, p.338, 538–539, (1986); Charache, *Experientia.* 49: 126 (1993)).

Additionally, if the targeted nucleic acid region is a host-nucleic acid-integrated viral gene that is critical to the virus' further infectivity, the viral gene could be rendered ineffective or could be replaced by a donor nucleic acid which would be fatal to the host cell.

Further uses include restoration or destruction of gene function in experimental cell lines such as immortalizing cell lines by eliminating the function of cell cycle control genes, p53, retinoblastoma, or Waf-1/cip1 proteins; preparing animals lacking the function of particular genes (so-called "knockout" animals) for research; and site-directed mutagenesis to study the effect of altered proteins in vivo.

The present invention may be used in plant agriculture by increasing the protein nutrition of grains and other food plants; adding genes with new functions such as insect resistance; and increasing the expression of other genes with useful agricultural properties.

The use of and useful and novel features of mutagen-linked third strands to stimulate homologous recombination with a donor nucleic acid (third-strand-directed homologous recombination) will be further understood in view of the following non-limiting examples.

EXAMPLE 1

Homologous Recombination

This example serves as a demonstration of the general strategy for using mutagen-linked third-strands to stimulate specific site homologous recombination with a donor nucleic acid. The strategy is illustrated schematically in FIG. 1, where the process of recombination resulting in a wild type supF gene is illustrated. The results are summarized in Table 1 below.

Homologous recombination assay.

The design of an assay system to study targeted recombination in an SV40 vector in monkey COS cells is shown in FIG. 1. In addition to the SV40 sequences necessary to enable replication in mammalian cells, the SV40 shuttle vector contains the supF gene, a suppressor tRNA gene of *E. coli*, as the target gene for effecting DNA damage. It also contains the pBR327 replication origin and β-lactamase gene for growth and selection in bacteria.

The SV40 vector DNA containing a mutant supF gene, supF163, is incubated with the psoralen-linked oligonucleotides, either pso-AG10 SEQ ID NO: 2, pso-AGT30 SEQ ID NO: 1, or control oligonucleotides (including Mix30 SEQ ID NO: 3), AG10 SEQ ID N: 2 and AGT30 SEQID NO: 1 are designed to bind to supF gene sequences such that the psoralen is delivered to the intended intercalation site at bp 166–167. After allowing time for triplex formation, the DNA is irradiated with UVA to activate the psoralen to form photoadducts and consequently DNA damage at the targeted site SEQ ID NO: 4 in the supF gene. The vector DNA and the wild type supF donor fragment are co-transfected into the cells. Another 48 hours are allowed for homologous recombination and vector replication to take place. The vector DNA is harvested from the cells by an alkaline lysis procedure and used to transform lacZ (amber) *E. coli* to detect a wild type supF gene resulting from homologous recombination that occurred in the COS cells (FIG. 1). Prior to transformation, Dpn I digestion of the vector DNA is used to eliminate unreplicated vector molecules lacking the mammalian methylation pattern.

Construction of novel supF genes.

In order to develop an assay system to more thoroughly examine parameters governing in vivo triplex formation and targeting of DNA damage, modified supF genes were constructed which contained polypurine and polypyrimidine segments amenable to triplex formation. We sought to incorporate into these synthetic supF genes novel sequences so that a series of potential triplex-forming oligonucleotides could be tested while still using bp 166–167 as the targeted psoralen intercalation site, since we have shown that mutations at this site produce detectable changes in supF function (Havre, et al., *Proc. Natl. Acad. Sci. USA* 90:7879 (1993); Havre and Glazer, *J. Virology*, 67:7324 (1993)).

Figure 2:
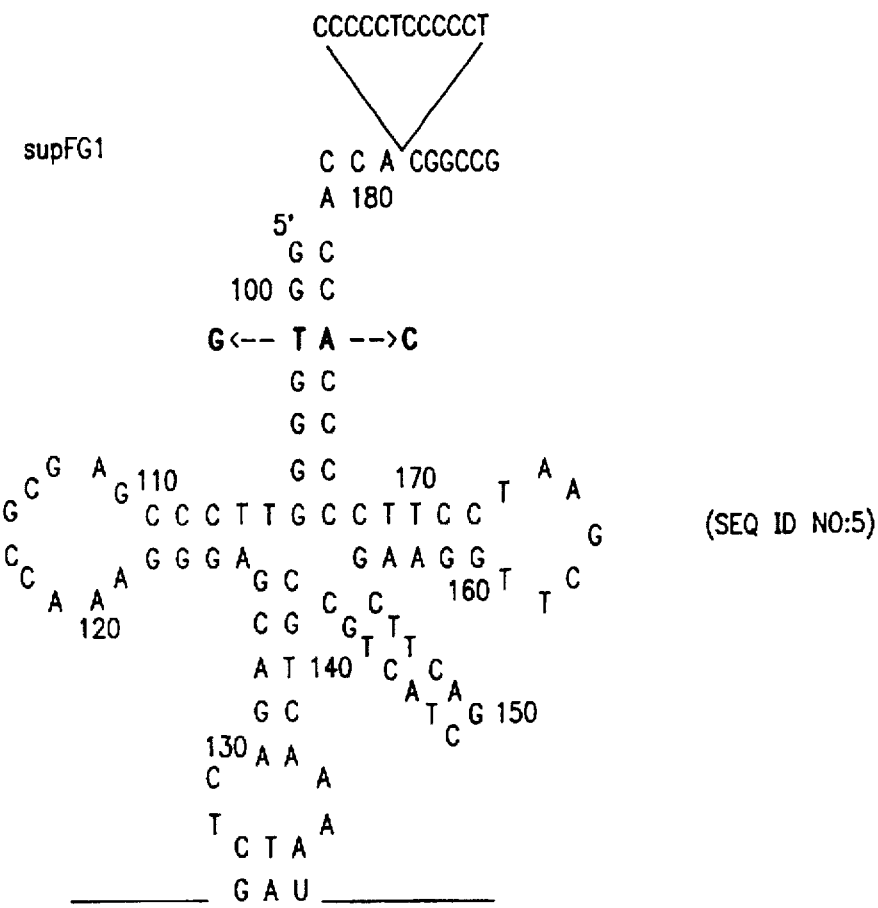
FIG. 2 depicts a modified supF reporter gene.

In order to construct a modified supF gene, we took advantage of the design of the pSP189 vector, in which a 93 bp segment encompassing the sequences coding for the mature tRNA is included between unique Xho I and Eag I sites. Using synthetic oligonucleotides, this 93 bp stretch can be replaced with novel sequences. The design of one new supF gene, supFG1 SEQ ID NO: 5, is illustated in FIG. 2. To eliminate one interruption at bp 177 in the polypurine-:polypyrimidine run, an A:T to C:G transversion was incorporated into the synthetic fragment, along with a compensatory T:A to G:C change at bp 101 to maintain base pairing in the amino acid acceptor stem of the mature tRNA. In addition, a 12 bp polypurine:polypyrimidine sequence was inserted between bp 183 and 184 to extend the length of the polypurine:polypyrimidine run in the gene to 30 bp. Since the 5'-CCA-3' sequence at positions 181–183 constitutes the 3' terminal amino acid acceptor site of the tRNA, the new sequences 3' to position 183 do not affect the mature tRNA molecule and so do not alter the phenotype of the gene. Following annealing and ligation of the synthetic oligonucleotides into the vector, constructs containing functional suppressor genes were identified by transformation of lacZ (amber) bacteria (Parris, et al., *J. Mol. Biol.* 236:491 (1994)). The sequence of the new supFG1 gene was confirmed by direct DNA sequencing of the vector DNA. The new construct contained a 30 bp polypurine site with just 2 interruptions (Table 1 and FIG. 5). To create a recipient gene to study recombination, a C:G to G:C mutation was introduced at position 163, inactivating function of the gene, and yielding the new gene, supF163.

Construction of 2600 base-pair double-stranded supF genes to serve as donor for homologous recombination.

The 2600 bp HindIII fragment from pSupFG1 was cut out from the plasmid DNA and gel purified by standard methods.

Third-strand-directed homologous recombination in vivo.

Using pSupF163 as a target vector, we carried out experiments to study DNA damage targeting and induced recombination by the psoralen-linked oligonucleotide pso-AGT30, which was designed to form a triple helix with the sequence in supFG1 and to deliver the tethered psoralen to bp 166–167. The results are shown in Table 1, below.

TABLE 1

| Reaction | Recombination (% blue colonies) |
| --- | --- |
| 1. pSupF163 alone | 0.0 (0/400) |
| 2. pSupF163, pso-AGT30 SEQ ID NO:1 | 0.15 (1/687) |

TABLE 1-continued

| Reaction | Recombination (% blue colonies) |
| --- | --- |
| 3. pSupF163, pso-AGT30 SEQ ID NO:1 and wild type fragment | 36.3 (246/678) |
| 4. pSupF 163 and wild type fragment | 12.8 (82/642) |

In these experiments, the vector DNA was incubated for 2 hours with the pso-AGT30 oligonucleotide and then irradiated with UVA. The vector DNA was co-transfected into the COS cells with an 1:1 ratio of a 2600 bp fragment from the pSupFG1 plasmid containing the wild type supFG1 gene. Controls included: (1) the vector DNA alone was transfected; (2) the vector plus pso-AGT30 SEQ ID NO: 1 plus UVA but no donor fragment were transfected (to measure posible damage induced reversion of the 163 mutation); (3) the vector plus the donor fragment but no triplex-forming oligonucleotide (to determine the extent of recombination in the absence of site specific damage stimulation). The extent of recombination in the supF163 gene induced by the triplex-delivered psoralen damage was 36.3% compared to the 12.8% for the background control. These results demonstrate third-strand-directed homologous recombination within cells. However, the background frequency is quite high in the experiment, in part because the donor fragment can circularize and subsequently replicate, contributing to the high background.

EXAMPLE 2

Recombination Stimulated in Vivo

Figure 3:
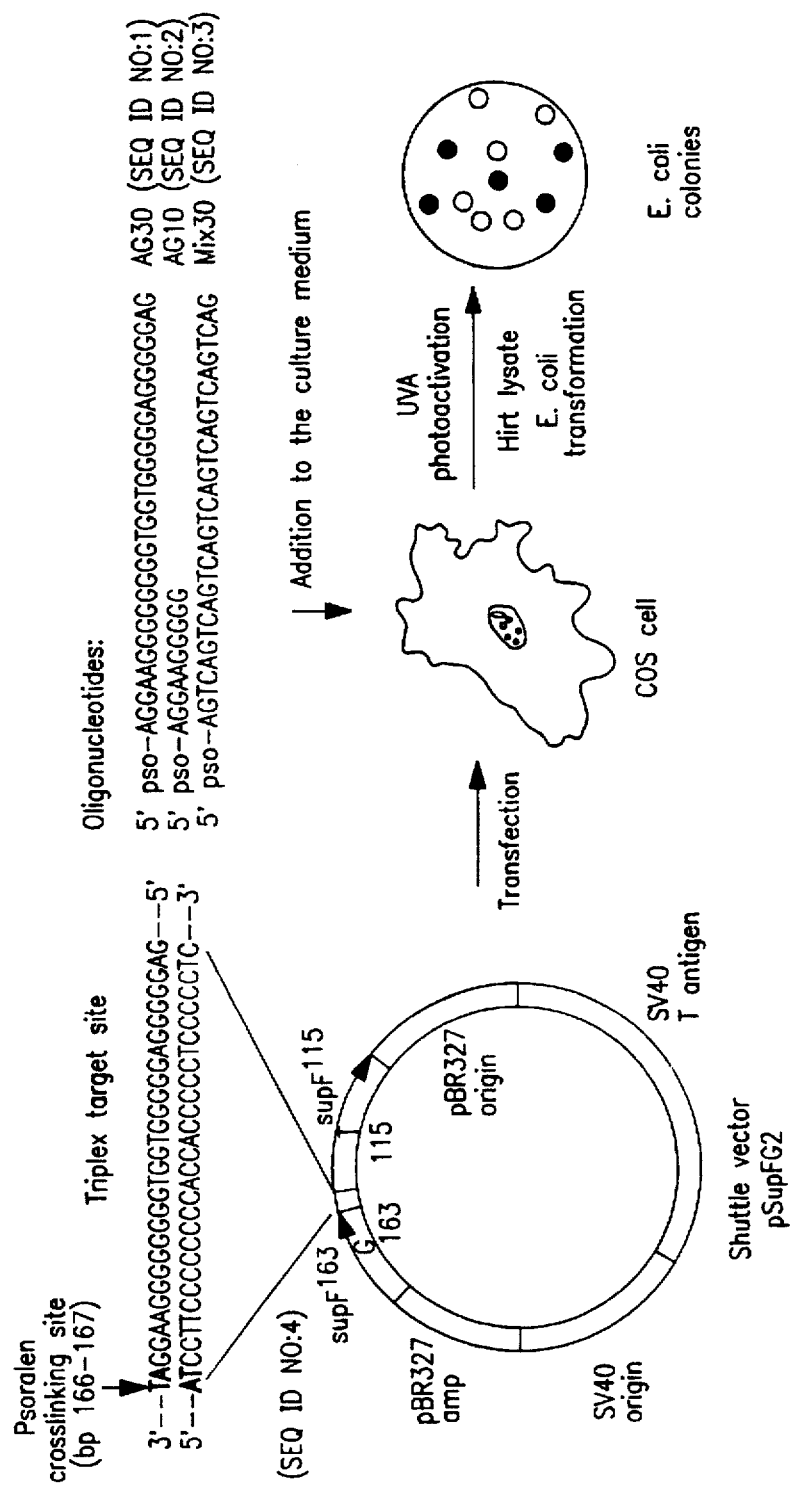
FIG. 3 schematically illustrates the experiment demonstrating intramolecular homologous recombination in COS cells.

The present example shows that triple helix forming oligonucleotides can enter cells, find and bind to their target sites, and mediate the stimulation of homologous recombination in vivo. As shown in FIG. 3, a new vector was constructed in which two supF genes were arranged in tandem, in the same 5' to 3' orientation with respect to the coding strand of the gene. The two supF genes were both mutated, but at different positions, bp 163 and bp 115, as shown, so that neither coded for a functional gene. Between the two genes, a 30 base pair triplex binding site was included. This is a site to which pso-AGT30 binds with high affinity (Kd=3×10$^{-9}$ M).

The COS cells were transfected with the vector (pSupF2) by electroporation. One hour later, the cells were exposed to the oligonucleotides, either pso-AGT30 SEQ ID NO: 1 (which binds with high affinity) or pso-Mix30 SEQ ID NO: 3 (which does not bind at all). Two hours later, the cells were irradiated with UVA. After 48 hours, the cells were lysed, and the viral vector genomes were isolated for genetic analysis. The reconstruction of a functional supF gene (via recombination) is detected by a blue bacterial colony in the shuttle vector assay. The results are shown in Table 2. Pso-AGT30 SEQ ID NO: 1 induced a recombination frequency of 1.5% via in vivo triplex formation. The other oligo (pso-Mix30) SEQ ID NO: 3, which does not bind, was ineffective, consistent with the hypothesis that intracellular triplex formation and damage-induction can stimulate homologous recombination. The vector alone had a low level of spontaneous recombination.

TABLE 2

| Oligonucleotide | Recombination Frequency |
|---|---|
| None | ≤0.03% |
| pso-AGT30 SEQ ID NO:1 | 1.5% |
| pso-Mix30 SEQ ID NO:3 | 0.06% |

The details of materials and methods for this example are as follows:

Oligonucleotides and vectors.

Psoralen-linked oligonucleotides were obtained from Oligos Etc. (Wilsonville, Oreg.) or were synthesized by J. Flory of the W. M. Keck Biotechnology Resource Center at Yale using materials from Glen Research (Sterling, Va.). The psoralen is incorporated into the oligonucleotide synthesis as a psoralen phosphoramidite, resulting in an oligonucleotide linked at its 5' end via a two-carbon linker arm to 4'-hydroxymethyl-4,5 ',8-trimethylpsoralen. The sequence of the psoralen-conjugated oligonucleotide used in this example is illustrated in FIG. 3. The psoralen-conjugated oligonucleotide was also synthesized to contain a 3' propylamine group (available as an amino-CPG for automated oligonucleotide synthesis from Glen Research) to minimize susceptibility to degradation by 3' exonucleases (Orson, et al., *Nucleic Acids Res.*, 19:3435 (1991)).

SV40 shuttle vector, pSupFG1 is a derivative of pSP189 (Parris and Seidman, Gene, 117:1 (1992)) and carries a new triplex binding site within a modified supF gene engineered into the parent plasmid (See Wang, et al., *Molecular and Cellular Biology*, 15:3, pp. 1759–68 (March, 1995), the contents of which is incorporated by reference). The sequence of the putative triplex binding sites in the new supFG1 gene is listed in FIG. 2 (SEQ ID NO: 6).

DNA damage protocol.

Monkey COS-7 cells were obtained from the ATCC (1651-CRL). The COS cells at 70% confluence were washed with PBS-EDTA, treated with trypsin, and incubated at 37° C. for 5 minutes. The cells were resuspended in DMEM/10% FCS and were washed three times by centrifugation at 900 rpm for 5 minutes (4° C.) using a Sorvall RT6000D. The cells were finally resuspended at $1 \times 10^7$ cells/ml. The plasmid DNAs were added at 3 µg DNA/$10^6$ cells and the cell/DNA mixtures were left on ice for 10 minutes. Transfection of the cells was performed by electroporation using a Bio-Rad gene pulser at a setting of 25 µF / 250 W / 250 V in the 0.4 cm cuvette. Following electroporation, the cells were kept on ice for 10 minutes.

The cells were diluted with growth medium, washed, and transferred to 37° C. for 30 minutes. At this point, the cells were further diluted and exposed to the oligonucleotides in growth medium at the indicated concentration while in suspension.

The suspension samples were incubated at 37° C. with gentle agitation every 15 minutes. UVA irradiation was given 2 hours later at a dose of 1.8 J/cm². All samples, including control cells not exposed to oligonucleotides, received UVA irradiation. The cells were further diluted in growth medium and allowed to attach to plastic dishes at a density of $2 \times 10^4$ cells per cm². The cells were harvested 48 hours later for vector analysis.

Shuttle vector isolation and analysis.

The cells were harvested for vector DNA isolation using a modified alkaline lysis procedure. The cells were detached by trypsinization, washed, and resuspended in 100 µl of cell resuspension solution (50 mM Tris/HCl, 10 mM EDTA, pH8.0; 100 µg/ml RNase A). An equal volume of cell lysis solution (0.2M NaOH, 1% SDS) was added, followed by 100 µl of neutralization solution (3M potassium acetate, pH 5.5). A 15 min room temperature incubation was followed by centrifugation in a microcentrifuge for 10 minutes. The supernatant was extracted with an equal volume of phenol/chloroform (1:1) once, and the DNA was precipitated with 2.5 volumes of ethanol at −70° C. for 10 minutes. The DNA was collected by centrifugation for 10 minutes, washed with 70% ethanol once, and allowed to air dry for 5 minutes at RT. The DNA was digested with Dpn I and RNase A at 37° C. for 2 hours, extracted with phenol/chloroform, and precipitated with ethanol. The DNA pellet was dissolved in 10 µl of TE buffer, and 1 µl of the sample of vector DNA was used to transform either *E. coli* SY204 [lacZ125(amber)] (14,15) or MBM7070 [lacZ(amber)] (Parris and Seidman, Gene, 117:1 (1992); Parris, et al., *J. Mol. Biol.* 236:491 (1994)) by electroporation (Bio-Rad, setting 25 µF / 250 W / 1800 V, using a 0.1 cm cuvette). The transformed *E. coli* cells were plated onto LB plates containing 50 µg/ml of ampicillin, 100 µg/ml of X-gal, and 1 µM IPTG and were incubated at 37° C. overnight. Colonies containing reconstructed, wild type supF genes able to suppress the amber mutation in the host cell β-galactosidase gene were detected as blue colonies among the mutant white ones. The blue colonies and the total colonies were counted, and the proportion was taken as an indication of the recombination frequency.

EXAMPLE 3

Specificity of DNA damage induction

Figure 4:
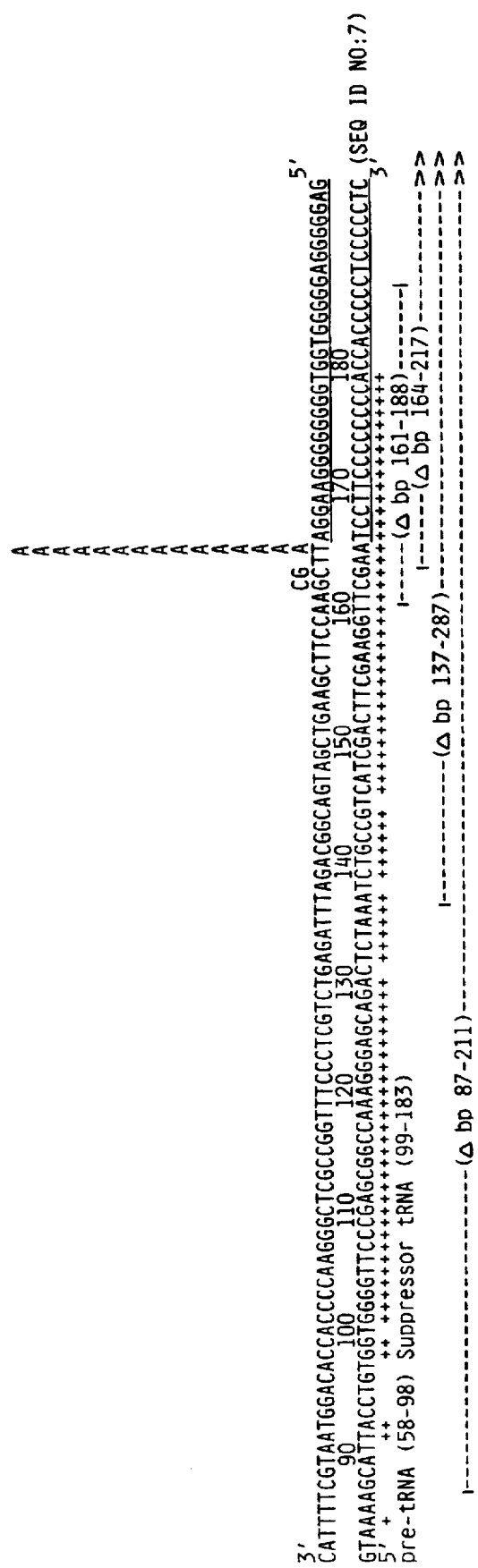
FIG. 4 shows the results of sequence analysis of mutations targeted in vivo within COS cells to the supFG1 gene in the SV40 vector by a psoralen-conjugated, triple-stranded-helix forming oligonucleotide pso-AGT30.

Sequencing to identify mutations provides a "footprint" of previous DNA damage that has escaped repair; and therefore, it serves as evidence of third-strand binding and DNA damage specifically at the targeted site. FIG. 4 shows the results of sequence analysis of mutations targeted in vivo within COS cells to the supFG1 gene in the SV40 vector by a psoralen-conjugated, triple-stranded-helix forming oligonucleotide pso-AGT30 SEQ ID NO: 1. In these experiments, the cells were transfected with the pSupFG1 vector and subsequently exposed to the oligonucleotide, followed by UVA irradiation. Rather than recombination, forward mutations were assayed. Note that no mutation has occurred at bases more than three bases from the targeted thymine base, which indicates the high specificity of DNA damage, and therefore, high specificity of this approach for the induction of recombination-stimulating damage.

In FIG. 4, point mutations produced by pso-AG30 SEQ ID NO: 1 and UVA treatment of the vector-containing cells are indicated above each base pair, with the listed base representing a change from the sequence in the top strand. Deletion mutations are represented below the supFG1 SEQ ID NO: 7 sequence, indicated by the dashed lines. The +signs below the sequence are sites in the supF gene at which mutations are known to produce a detectable phenotype change (Kraemer and Seidman, *Mutat. Res.*, 220:61 (1989)), which demonstrates that the use of supF in this assay does not bias detection of mutations at any particular site. The underlined nucleotides delineate the site targeted for triple-stranded helix formation.

The procedures used to create the mutant supF genes are presented in Example 1, with the additional experimental protocol described below:

DNA sequencing.

The mutant colonies were purified and the plasmids were isolated for DNA sequence analysis. The purified mutant colonies were picked into 5ml of L broth containing ampicillin (50 μg/ml) and were incubated at 37° C. for 16–20 hours by shaking at 250 rpm. Cells from 3 mls of culture were collected by centrifugation. Isolation of plasmid DNA was accomplished using the Wizard plasmid miniprep DNA purification system (Promega, Madison, Wis.). Plasmid DNA was sequenced using an Applied Biosystems cycle-sequencing kit as directed by the manufacturer. The sequencing primer was chosen to bind to the β-lactamase gene just upstream of the supF gene in the vector (Parris and Seidman, *Gene*, 117:1 (1992); Parris, et al., *J. Mol. Biol.*, 236:491 (1994)).

EXAMPLE 4

Concentration Dependence of Mutagenesis and Reduced Toxicity

Mutagenesis provides a "footprint" of previous DNA damage that has escaped repair; and therefore, it serves as evidence of third-strand binding and DNA damage specifically at the targeted site. The amount of DNA damage greatly exceeds the amount evidenced by mutagenesis footprints, since most damage is repaired.

The concentration dependence of percent third-strand-directed mutagenesis is presented in Table 3. The data in the table provide evidence for a number of desirable features of the invention: The maximum percent mutagenesis, 2.1%, indicates that third-strands enter the cell and cause a significant amount of DNA damage (minimum 2.1%). Third-strands can deliver typical therapeutic amounts of a drug, 2,000 nM, without toxicity; and that third-strands render psoralen less toxic than when administered in the free state (i.e., not attached to third strands).

Psoralen when delivered in the free state is normally toxic to cells at 1-10 nM, so attachment to third strands reduces its toxicity by approximately 1000 to 10,000-fold, a fact of interest for therapeutic utility, research applications, and genetic engineering applications. This phenomenon is not unique to psoralen. For example, an acridine orange-conjugated oligonucleotide at 50-100 mM does not cause toxicity in MDCK cells to which they were exposed three days. In contrast, free acridine orange at only 2 mM caused toxicity in the same cells after the same exposure (Zerial, et al., *Nucleic Acids Res.*, 15: 9909 (1987)).

Experimental protocols are as decribed in Example 1, with the following additional protocols:
Concentration dependence.

Following electroporation of the COS cells with the SV40 vector DNA, the cells were incubated in suspension in the presence of pso-AGT30 SEQ ID NO: 1 at concentrations from 1 nM to 2 μM. UVA irradiation was given 2 hours later. Although we have not directly measured the intracellular oligonucleotide concentration in these experiments, other studies have reported that treatment of mammalian cells with oligonucleotides produces concentrations within cells that are in the same range as or even higher than the given extracellular concentrations (Ing, et al., *Nucleic Acids Res.*, 21:2789 (1993); Orson, et al., *Nucleic Acids Res.*, 19:3435 (1991)). A low level of mutagenesis, just slightly above background, was observed when the extracellular oligonucleotide concentration was in the 1 to 100 nM range. Significant mutagenesis was seen at concentrations in the 450 nM to 2 μM range (mutation frequencies from 1.0 to 2.1%). We also tested a concentration of 10 μM pso-AGT30 SEQ ID NO: 1. At this high concentration, some cellular toxicity was observed following UVA irradiation, presumably due to the psoralen participating in secondary photoreactions with cellular macromolecules. The frequency of mutations observed in this case fell to 0.4%, probably because of this toxicity. These results are summarized in Table 3.

TABLE 3

| Oligo nucleotide | Concentration (nM) | Mutation frequency (%) | Mutant/ total |
|---|---|---|---|
| none | 0 | 0.05 | 2/3,940 |
| pso-AGT30 SEQ ID NO:1 | 1 | 0.1 | 3/3,100 |
| " | 10 | 0.2 | 5/2,425 |
| " | 100 | 0.2 | 8/3,625 |
| " | 450 | 1.0 | 51/5,175 |
| " | 1,000 | 1.1 | 37/3,400 |
| " | 2,000 | 2.1 | 178/8,663 |
| " | 10,000 | 0.4 | 8/2,200 |

EXAMPLE 5

Time Dependence of Third-Strand-Directed DNA Damage

In this example, mutagensis is used as a footprint for evidence of previous DNA damage. The time course of mutagenesis lags the time course of DNA damage, but will set a minimum for the time that DNA damage occurs.

The time-course dependence of percent third-strand-directed mutagenesis is presented in Table 4. The data in the table illustrate a desirable feature of the invention, namely that the maximum mutation frequency is observed in about 2 hours, which is a favorable time from a pharmacokinetic point of view. That is, the typical 8-hour half-life of oligonucleotides in tissue indicates that there is ample time for an injected mutatagen-linked-third strand to damage its target.

TABLE 4

| Oligo-nucleotide | Time (hours) | Mutation frequency (%) | Mutant/ total |
|---|---|---|---|
| none | n.a. | 0.08 | 3/3,900 |
| pso-AGT30 SEQ ID NO:1 | 1 | 0.2 | 7/3,275 |
| " | 2 | 1.4 | 25/1,825 |
| " | 4 | 0.7 | 14/2,150 |
| " | 8 | 0.1 | 4/3,850 |

Experimental protocols are as decribed in Example 1, with the following additional protocols:
Time course of UVA irradiation.

We next sought to investigate the kinetics of intracellular targeted mutagenesis mediated by third-strand-directed DNA damage. This process depends on the entry of the oligonucleotides into the cells, migration into the nucleus, and specific binding to the triplex target site. In order to achieve targeted mutagenesis via site-specific generation of a psoralen photoadduct, these steps must occur by the time the UVA irradiation is given. A time course experiment was carried out in which the time of UVA irradiation following pso-AGT30 addition to the cells was varied.

The cells, allowed to attach as a monolayer immediately after electroporation, were used in two different time course experiments. In one, the cells, as an attached monolayer, were incubated in the presence of the oligonucleotides added to the growth medium of the culture dish at a concentration of 2μM. At various times following oligonucleotide addition, the cells were washed with PBS and irradiated with UVA light. Fresh growth medium was added, and the cells were harvested 48 hours later for analysis. A control was also run which received UVA irradiation, but no oligonucleotide addition.

In the results shown in Table 4, the cells were electroporated with the pSupFG1 vector, washed, diluted with growth medium, and allowed to attach as a monolayer in the culture dish before addition of the oligonucleotide to the culture medium. The cells were treated as a monolayer rather than maintained in suspension for this experiment because prolonged incubation of the COS cells in suspension leads to cell aggregation. UVA irradiation was given at the indicated times. As the interval between oligonucleotide addition and UVA irradiation was increased, the yield of targeted mutations initially increased, with a frequency as high as 1.4% for the 2 hour point. However, at the later time points, the yield of mutations decreased, probably due to the degradation of the oligonucleotide within the cells, even though the oligonucleotides used were synthesized to contain a 3' propylamine to inhibit 3' exonuclease activity (Ing, et al., *Nucleic Acids Res.*, 21:2789 (1993); Orson, et al., *Nucleic Acids Res.*, 19:3435 (1991)). The results indicate that at least 1 to 2 hours are required for cellular uptake of the oligonucleotides and for intracellular triplex formation.

Time course of oligonucleotide treatment.

In the above experiments, the cells were exposed to the third strand within 1 hour after introduction of the SV40 vector DNA by electroporation. Although transfected SV40 vectors become covered in chromatin upon introduction into monkey cells (Cereghini and Yaniv, *EMBO J*, 3:1243 (1984)), we were concerned that, at such an early time point, this process might be incomplete. We carried out an experiment in which the cells were transfected with pSupFG1, allowed to attach to dishes in growth medium, and incubated for 12 hours. The cells were then detached by trypsinization, washed 3 times in growth medium, and incubated in suspension in the presence of 2 µM pso-AGT30 for 2 hours before irradiation with UVA. In this experiment, mutations were generated in the supFG1 gene at a frequency of 1.5% (150 / 10,175), in the same range as seen when the cells are exposed to 2 µM pso-AGT30 within 1 hour after SV40 transfection (2.1%, Table 3). Hence, even with more than enough time allowed for chromatin assembly on the SV40 vector DNA, the psoralen-conjugated oligonucleotide can still generate targeted mutations in the supFG1 gene within the vector. This provides evidence that triplex formation can occur within chromatin.

---

What is claimed is:

1. A method for effecting homologous recombination between a native nucleic acid segment in a cell and a donor nucleic acid segment introduced into the cell, which comprises:

a) introducing into a cell: i) an oligonucleotide third strand which comprises a base sequence capable of forming a triple helix at a binding region on one or both strands of a native nucleic acid segment in the vicinity of a target region where the recombination is to occur, said oligonucleotide being capable of inducing homologous recombination at the target region of the native nucleic acid, and ii) a donor nucleic acid which comprises a nucleic acid sequence sufficiently homologous to the native nucleic acid segment such that the donor sequence is capable of undergoing homologous recombination with the native sequence at the target region;

b) allowing the oligonucleotide to bind to the native nucleic acid segment to form a triple stranded nucleic acid, thereby inducing homologous recombination at the native nucleic acid segment target region; and c) allowing homologous recombination to occur between the native and donor nucleic acid segments wherein the oligonucleotide third strand has a dissociation constant for the binding region of less than or equal to about $10^{-7}$ M.

2. The method of claim 1, wherein the oligonucleotide third strand is from about 7 to about 50 nucleotides in length.

3. The method of claim 2, wherein the oligonucleotide third strand is from about 10 to about 30 nucleotides in length.

4. The method of claim 1, wherein the oligonucleotide third strand contains an at least partially artificial backbone.

5. The method of claim 1, wherein the oligonucleotide third strand contains a backbone selected from the group consisting of phosphodiester, phosphorothioate, methyl phosphonate, peptide, and mixtures thereof.

6. The method of claim 5, wherein the backbone is phosphodiester.

7. The method of claim 1, wherein the oligonucleotide third strand is modified with one or more protective groups.

8. The method of claim 7, wherein the 3' and 5' ends of the oligonucleotide third strand are modified with one or more protective groups.

9. The method of claim 7, wherein the protective group is selected from the group consisting of alkyl amines, acridine and cholesterol.

10. The method of claim 1, wherein the oligonucleotide third strand is circularized.

11. The method of claim 1, wherein the oligonucleotide third strand contains at least one modified sugar.

12. The method of claim 1, wherein the oligonucleotide third strand comprises at least one synthetic base.

13. The method of claim 1, wherein the dissociation constant is less than or equal to about $2 \times 10^{-8}$ M.

14. The method of claim 1, wherein the oligonucleotide third strand has linked thereto a moiety which induces the homologous recombination.

15. The method of claim 14, wherein the moiety is linked to the oligonucleotide directly.

16. The method of claim 14, wherein the moiety is linked to the oligonucleotide through a linker.

17. The method of claim 14, wherein the moiety is selected from the group consisting of acridine, psoralen, a substituted psoralen, hydroxymethylpsoralen, mitomycin C, 1-nitrosopyrene, a nuclease, a restriction enzyme, a radionuclide, boron, and iodine.

18. The method of claim 1, wherein the donor nucleic acid is double stranded.

19. The method of claim 1, wherein the donor nucleic acid is single stranded.

20. The method of claim 1, wherein the donor nucleic acid comprises two substantially complementary single strands.

21. The method of claim 1, wherein the donor nucleic acid is substantially homologous with the native nucleic acid.

22. The method of claim 21, wherein the donor nucleic acid is substantially homologous with the native nucleic acid in a region of about 20 bases at each end of the donor nucleic acid.

23. The method of claim 1, wherein the donor nucleic acid is at least about 40 bases in length.

24. The method of claim 23, wherein the donor nucleic acid is between about 40 and about 40,000 bases in length.

25. The method of claim 1, wherein the donor nucleic acid is introduced into the cell in the form of a packaging system.

26. The method of claim 25, wherein the packaging system is selected from the group consisting of a DNA virus, an RNA virus, and a liposome.

27. The method of claim 1, wherein the native nucleic acid contains a mutation that is corrected by the homologous recombination.

28. The method of claim 27, wherein the mutation is selected from the group consisting of base changes, deletions, insertions, nucleotide repeats, and combinations thereof.

29. The method of claim 1, wherein the homologous recombination causes an alteration in the native nucleic acid sequence.

30. The method of claim 29, wherein the alteration is an addition of a segment selected from the group consisting of a gene, a part of a gene, a gene control region, an intron, a splice junction, a transposable element, a site specific recombination sequence, and combinations thereof.

31. The method of claim 1, wherein the native nucleic acid is chromosomal.

32. The method of claim 1, wherein the native nucleic acid is extrachromosomal.

33. The method of claim 32, wherein the native nucleic acid is selected from the group consisting of mitochondrial, episomal, a plasmid and a chloroplast.

34. A method for effecting homologous recombination between a first nucleic acid segment in a cell and a donor nucleic acid segment introduced into the cell, which comprises:

a) contacting a donor nucleic acid segment with an oligonucleotide third strand which comprises a base sequence capable of forming a triple helix at a binding region on one or both strands of the donor nucleic acid segment in the vicinity of a target region where the recombination is to occur, said oligonucleotide being capable of inducing homologous recombination at the target region of the donor nucleic acid, and said donor having a sequence sufficiently homologous to a first nucleic acid segment such that the donor sequence will undergo homologous recombination with the first sequence at the target region;

b) allowing the oligonucleotide to bind to the donor nucleic acid segment to form a triple stranded nucleic acid, thereby treating the donor nucleic acid segment to make it capable of inducing homologous recombination at the donor nucleic acid segment target region;

c) introducing into a cell the treated donor nucleic acid; and d) allowing homologous recombination to occur between the first and donor nucleic acid segments wherein the oligonucleotide third strand has a dissociation constant for the binding region of less than or equal to about $10^{-7}$ M.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AGGAAGGGGG GGGTGGTGGG GGAGGGGGAG        30

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGGAAGGGGG        10

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGTCAGTCAG TCAGTCAGTC AGTCAGTCAG        30

( 2 ) INFORMATION FOR SEQ ID NO:4:

( i ) SEQUENCE CHARACTERISTICS:

-continued

```
        ( A ) LENGTH: 31 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

ATCCTTCCCC  CCCCACCACC  CCCTCCCCCT  C                                31

( 2 ) INFORMATION FOR SEQ ID NO:5:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGTGGGGTTC  CCGAGCGCCA  AAGGGAGCAG  ACTCTAAAAC  TGCCGTCATC          50

GACTTCGAAG  GTTCGAATCC  TTCCCCCACC  ACCACCCCCT  CCCCTCGGC          100

CG                                                                 102

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TCCTTCCCCC  CCCACCACCC  CCTCCCCCTC                                  30

( 2 ) INFORMATION FOR SEQ ID NO:7:

( i ) SEQUENCE CHARACTERISTICS:
        ( A ) LENGTH: 115 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:7:

GTAAAAGCAT  TACCTGTGGT  GGGGTTCCCG  AGCGGCCAAA  GGGAGCAGAC          50

TCTAAATCTG  CCGTCATCGA  CTTCGAAGGT  TCGAATCCTT  CCCCCCCCAC         100

CACCCCCTCC  CCCTC                                                  115
```